(12) United States Patent
Zhou et al.

(10) Patent No.: US 7,375,132 B2
(45) Date of Patent: May 20, 2008

(54) COMPOUNDS AND METHODS FOR INHIBITING CELLULAR RESPONSES TO HYPOXIA

(75) Inventors: Yu-Dong Zhou, Oxford, MS (US); Dale G. Nagle, Oxford, MS (US); Asjad Kaleem Mohammed, University, MS (US); Chowdhury Faiz Hossain, University, MS (US)

(73) Assignee: University of Mississippi, University, MS (US)

( * ) Notice: Subject to any disclaimer, the term of this patent is extended or adjusted under 35 U.S.C. 154(b) by 258 days.

(21) Appl. No.: 11/083,371

(22) Filed: Mar. 18, 2005

(65) Prior Publication Data

US 2006/0058377 A1   Mar. 16, 2006

Related U.S. Application Data

(60) Provisional application No. 60/554,975, filed on Mar. 19, 2004.

(51) Int. Cl.
*C07D 311/00* (2006.01)
*A61K 31/35* (2006.01)

(52) U.S. Cl. ...................... 514/456; 549/397
(58) Field of Classification Search ............... 549/397; 514/456
See application file for complete search history.

(56) References Cited

U.S. PATENT DOCUMENTS 5,347,007 A   9/1994   Das et al.

OTHER PUBLICATIONS

McGraw—Hill Dictionary of Chemical Terms, pp. 200, 1987.*
Concise Encylopedia Chemistry, pp. 490, 1993.*
Hawley's Condensed Chemical Dictionary, 594, 1993.*
U.S. Appl. No. 10/842,177, filed May 10, 2004, Nagle, et al.
Wessels, et al.; *New Natural Product Isolation and Comparison of the Secondary Metabolite Content of Three Distinct Samples of the Sea Hare Aplysia dactylomela from Tenerife*; J Nat. Prod.; 2000; 63; pp. 920-928.
Mohammed, et al.; *Leurenditerpenol, a New Diterpene from the Tropical Marine Alga Laurencia intricate that Potently Inhibits HIF-1 Mediated Hypoxic Signaling in Breast Tumor Cells*; J. Nat. Prod., 2004, 67, pp. 2002-2007.

* cited by examiner

*Primary Examiner*—Janet L. Andres
*Assistant Examiner*—Raymond Covington
(74) *Attorney, Agent, or Firm*—Stites & Harbison PLLC; Richard S. Myers, Jr.

(57) ABSTRACT

Compounds and compositions of the following formula:

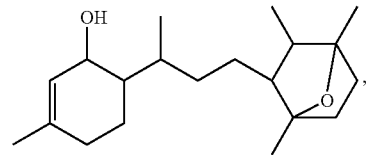

and analogs and stereoisomers thereof (and pharmaceutically acceptable carriers). Additionally disclosed is a method of inhibiting hypoxia-inducible factor-1 function in a patient or sample thereof, comprising administering to the patient or sample an effective inhibiting amount of a compound or composition of the present invention.

12 Claims, 5 Drawing Sheets

COMPOUNDS AND METHODS FOR INHIBITING CELLULAR RESPONSES TO HYPOXIA

PRIORITY

This invention claims benefit under 35 U.S.C. § 119(e) to U.S. Patent Application Ser. No. 60/554,975, filed Mar. 19, 2004 the contents of which are incorporated herein by reference in their entirety.

GOVERNMENT SUPPORT

This invention was made with support from Grant Number DAMD 17-01-0566 from the Department of Defense and CA 98787-01 from the National Institutes of Health. The Government has rights to this invention.

FIELD OF THE INVENTION

The present invention relates generally to the field of compounds and compositions that exhibit the ability to inhibit hypoxia-inducible factor-1 function. The present invention also relates to methods of inhibiting hypoxia-inducible factor-1 function. Specific inhibitors of HIF-1 can be useful for the prevention and treatment of cancer, stroke, heart disease, diabetic retinopathy, age-related macular degeneration, and arthritis. The compounds of the present invention are also useful as anti-tumor, anti-angiogenic, and cytoprotective agents.

BACKGROUND OF THE INVENTION

Gene regulation (selective activation and inactivation of genes) plays an important role in the development and progression of cancer, an assemblage of diseases that result from multiple accumulated mutations. The past two decades have witnessed the rapid expansion of our knowledge of cancer genetics, from a handful of oncogenes to the identification of many genes that affect tumorigenesis, tumor growth, progression, metastasis, and tumor cell death. Elucidation of the molecular mechanisms underlying these events provides the opportunity to develop new mechanism-based therapeutics. As a result, the first molecular targeted agent (Trastuzumab) is in clinical use, and many molecular-based agents are in clinical trial.

An embodiment of the present invention is the discovery and characterization of potential chemotherapeutic agents that specifically target tumor hypoxia. The existence of hypoxic regions is a common feature of solid tumors. Unlike normal cells from the same tissue, tumor cells are often chronically hypoxic. The extent of tumor hypoxia correlates with advanced stages and poor prognosis. Rapid growth of tumors outstrips the capability of existing blood vessels to supply oxygen and nutrients, and remove metabolic waste. Hypoxia triggers tumor angiogenesis and the newly formed tumor blood vessels often fail to mature. As a result, certain tumor regions are constantly under hypoxic stress due to sluggish and irregular blood flow. Hypoxic tumor cells are more resistant than normoxic tumor cells to radiation treatment and chemotherapy and these hypoxic cells are considered an important contributor to disease relapse. Currently, the general strategies to overcome tumor hypoxia are: 1) increasing tumor oxygenation by means such as breathing carbogen (95% $O_2$, 5% $CO_2$); 2) developing chemical sensitizers to increase the sensitivity of hypoxic cells to radiation; and 3) developing hypoxic cytotoxins that selectively kill hypoxic cells. These approaches target the direct effects of hypoxia—lack of cellular oxygen. Presently, there is only one bioreductive drug (tirapazamine) in clinical trial that selectively kills hypoxic tumor cells. No hypoxic cytotoxins are currently approved. It is clear that tumor hypoxia is an important unmet therapeutic need for cancer treatment and drug discovery efforts should be directed at this target.

The focal point of this drug discovery effort is to target the important indirect effect of hypoxia—induction of genes that promote the adaptation and survival of tumor cells. As a form of stress, hypoxia activates both survival and cell death programs. In oncogenically transformed cells, hypoxia provides a physiological pressure and selects for the cells with diminished apoptotic potential. Hypoxic tumor cells that have adapted to oxygen and nutrient deprivation are associated with a more aggressive phenotype and poor prognosis. The transcription factor that plays a critical role in hypoxia-induced gene expression is Hypoxia-Inducible Factor-1 (HIF-1), a heterodimer of the bHLH-PAS proteins HIF-1α and HIF-1β/ARNT. HIF-1α protein is degraded rapidly under normoxic conditions and stabilized under hypoxic conditions, while HIF-1β protein is constitutively expressed. Upon hypoxic induction and activation, HIF-1 binds to the hypoxia response element (HRE) present in the promoters of target genes and activates transcription. Survival genes activated by HIF-1 can be classified into three major functional groups—(i) those that increase oxygen delivery through enhancing angiogenesis, erythropoiesis, and vasodilatation; (ii) those that decrease oxygen consumption through inducing numerous genes involved in anaerobic metabolism (glucose transporters and glycolytic enzymes); and (iii) growth factors. In addition to hypoxia, other tumor-specific mechanisms that increase HIF-1 activity include the activation of oncogenes (i.e. ras, src, myc, etc.) and the loss of tumor suppressor genes (i.e. PTEN, VHL). The oxygen regulated subunit HIF-1α protein is overexpressed in common human cancers and their metastases, and is associated with advanced stages in breast cancer. In animal models, deletion of either HIF-1α or HIF-1β blocks hypoxic induction of the genes that are normally induced by hypoxia, and is associated with reduced tumor vascularity and retarded tumor growth. In addition, inhibition of HIF-1 function through blocking the interaction between HIF-1 and the coactivator p300/CBP leads to an attenuation of hypoxia-inducible gene expression, reduction of angiogenesis, and suppression of both breast and colon carcinoma cell-derived tumor growth in vivo. In summary, results from multiple animal models indicate that inhibition of hypoxia-induced gene expression through blocking HIF-1 production/function is associated with significant suppression of tumor growth. Therefore, small molecule specific inhibitors of HIF-1 represent potential chemotherapeutic drugs that will suppress tumor growth, progression, and hypoxia associated treatment resistance by inhibiting hypoxia-induced gene expression.

SUMMARY AND OBJECTS OF THE INVENTION

Compounds and compositions of the following formula (I) and stereoisomers thereof exhibit the ability to potently and effectively inhibit hypoxia-inducible factor-1 function:

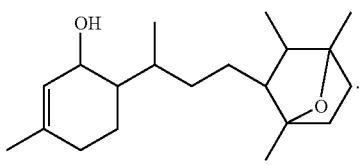

Formula (I)

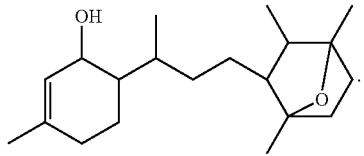

Formula (I)

Accordingly, such compounds and compositions effectively block hypoxia-activated tumor cell survival pathways and reduce angiogenic growth factor production in human breast tumor cells. In addition, HIF-1 activation is also associated with ischemic tissue damage, following vascular occlusion due to heart attack and stroke. Therefore, specific inhibitors of HIF-1 can be useful for the prevention and treatment of cancer, heart disease, and stroke. Further, the compounds and compositions of the present invention may enhance the activity of traditional chemotherapy and radiation treatments for cancer. Recent evidence suggests that HIF-1 inhibitors may be useful for the treatment of arthritis. Inhibitors of vascular endothelial growth factor (VEGF) are of potential utility in the treatment of diabetic retinopathy and age-related macular degeneration. VEGF is regulated by HIF-1 and the compounds and compositions of the present invention inhibit both HIF-1 and VEGF in tumor cell line. Therefore, these compounds may be useful in the treatment and prevention of diabetic retinopathy and macular degeneration.

Substances that inhibit HIF-1 function and available for the treatment of cancer, heart disease, stroke, arthritis, diabetic retinopathy, or macular degeneration are highly desired. Unlike conventional chemotherapy, selective HIF-1 inhibitors can specifically affect target tissues with a low level of non-selective cytotoxicity.

Accordingly, an object of the present invention is to provide compounds or pharmaceutical compositions of the compounds of the present invention described herein, including a compound of present invention including Formula (I).

Another object of the present invention is to provide methods of inhibiting HIF-1 function by administering to a patient in need thereof a pharmaceutically inhibiting amount of a compound of the present invention, including administration of a compound of the present invention including Formula (I).

Another embodiment of the present invention is to provide a method of treating cancer comprising administering a cancer treating effective amount of a compound of the present invention including Formula (I). The present invention can be used for the treatment of, for example, liver cancer, breast cancer, throat cancer, melanosis, lung cancer, prostate cancer, colon cancer, stomach cancer, cervical cancer, esophageal cancer, tongue cancer, oral cancer, pancreas cancer, thyroid cancer, leukemia and myeloma.

One object of the present invention is a compound of the following formula, and stereoisomers thereof:

Another object of the present invention is a method of inhibiting HIF-1 comprising administering a HIF-1 inhibiting amount of a compound of the present invention or a derivative thereof to a subject in need of such treatment. The compound may be administered as part of a formulation suitable for oral or non-oral administration. A pharmaceutical composition may be formed with the compounds of the present invention in the same manner that the compositions of Hahm et al., WO 01/87869, incorporated herein by reference, are prepared.

Another object of the present invention is a method of treating cancer, heart disease, stroke, chronic inflammatory diseases, arthritis, diabetic retinopathy, or macular degeneration, comprising administering an effective amount of a compound of the present invention, its derivative, or a pharmaceutically acceptable salt thereof.

Another object of the present invention is a method of treating ischemic tissue damage comprising administering an effective amount of a compound of the present invention, its derivative, or a pharmaceutically acceptable salt thereof.

Another object of the present invention is a method of inhibiting vascular endothelial growth factor (VEGF), comprising administering an effective amount of a compound of the present invention, its derivative, or a pharmaceutically acceptable salt thereof.

Additional objects of the present invention include enhancing the method of inhibiting and methods of treatment described herein.

With respect to all embodiments of the present invention, derivatives, stereoisomers, pharmaceutically acceptable salts, and analogs of compounds of the present invention, including Formula (I) are included. Specifically included are analogs where the methyl groups are substituted with substituted or unsubstituted chains such as alkyl or lower alkyl chains, or substituted or unsubstituted small rings, or substituted or unsubstituted heterocyclic rings that contain N, O, S, or carbon atoms. Furthermore, in embodiments of the present invention, the compounds of the present invention are substantially pure.

DETAILED DESCRIPTION OF THE INVENTION

Figure 1:
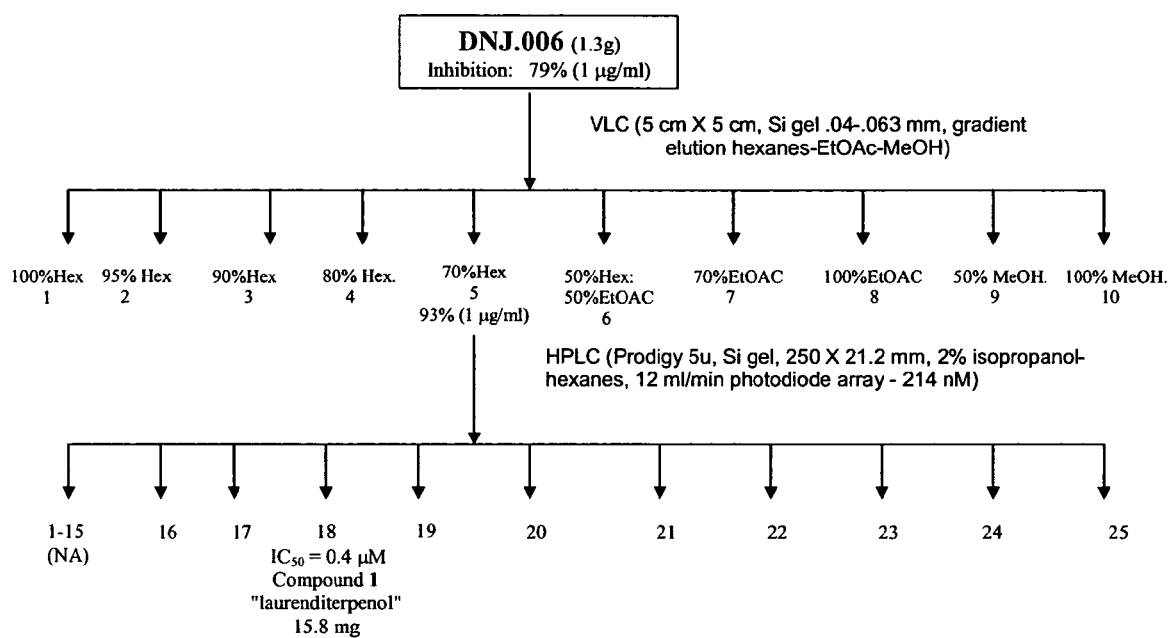
FIG. 1 shows a bioassay-guided fractionation used to help determine the chemical structure of a compound of the present invention.

As stated above, the compounds and compositions of the present invention exhibit the ability to inhibit hypoxia-inducible factor-1 function.

One compound of the present invention is a compound of the following formula:

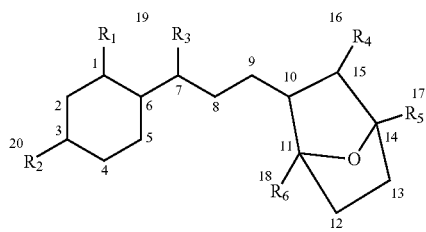

wherein $R_1$-$R_6$ are each independently H, substituted or unsubstituted alkyl, alkoxy, hydroxyl, heterocycle, amino, a closed carbon ring, or a bridge with a heteroatom; and the carbon atoms may for a double or triple bond with an adjacent carbon; and stereoisomers, analogs, and salts thereof.

Another embodiment of the present invention is a compound of the following formula:

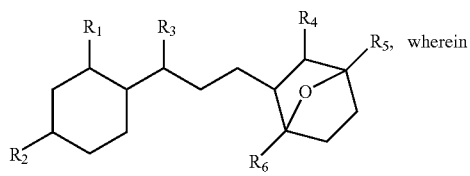

$R_1$-$R_6$ are each independently H, alkyl, alkoxy, hydroxyl, heterocycle, amino; and $R_1$ may form a cyclic alkyl group or a heterocyclic group, as defined herein, with at least one of $R_2$, $R_3$; and $R_4$ may form a cyclic alkyl group or a heterocyclic group, as defined herein, with at least one of $R_5$, $R_6$; and $R_5$ may form a cyclic alkyl group or a heterocyclic group, as defined herein, with $R_6$; and any carbon atom may form a double or triple bond with an adjacent carbon; and stereoisomers, pharmaceutically acceptable salts, and analogs thereof.

As discussed further below, the compounds of the present invention may be used in pharmaceutical compositions, comprising a compound of the present invention and a pharmaceutically acceptable carrier.

As used herein, the term alkyl or alkyl group is to be understood in the broadest sense to mean hydrocarbon residues which can be linear, i.e., straight-chain, or branched, and can be acyclic or cyclic residues or comprise any combination of acyclic and cyclic subunits. Further, the term alkyl as used herein expressly includes saturated groups as well as unsaturated groups which latter groups contain one or more, for example, one, two, or three, double bonds and/or triple bonds.

All these statements also apply if an alkyl group carries substituents or occurs as a substituent on another residue, for example, in an alkyloxy residue, or an arylalkylamino residue. Examples of alkyl residues containing from 1 to 20 carbon atoms are methyl, ethyl, propyl, butyl, pentyl, hexyl, heptyl, octyl, nonyl, decyl, undecyl, dodecyl, tetradecyl, hexadecyl, octadecyl, and eicosyl, the n-isomers of all these residues, isopropyl, isobutyl, 1-methylbutyl, isopentyl, neopentyl, 2,2-dimethylbutyl, 2-methylpentyl, 3-methylpentyl, isohexyl, 2,3,4-trimethylhexyl, isodecyl, sec-butyl, tert-butyl, or tert-pentyl.

Unsaturated alkyl residues are, for example, alkenyl residues such as vinyl, 1-propenyl, 2-propenyl (=allyl), 2-butenyl, 3-butenyl, 2-methyl-2-butenyl, 3-methyl-2-butenyl, 5-hexenyl, or 1,3-pentadienyl, or alkynyl residues such as ethynyl, 1-propynyl, 2-propynyl (=propargyl), or 2-butynyl. Alkyl residues can also be unsaturated when they are substituted.

Examples of cyclic alkyl residues are cycloalkyl residues containing 3, 4, 5, 6, 7, or 8 ring carbon atoms like cyclopropyl, cyclobutyl, cyclopentyl, cyclohexyl, cycloheptyl, or cyclooctyl which can also be substituted and/or unsaturated. Unsaturated cyclic alkyl groups and unsaturated cycloalkyl groups like, for example, cyclopentenyl or cyclohexenyl can be bonded via any carbon atom. The term alkyl as used herein also comprises cycloalkyl-substituted alkyl groups like cyclopropylmethyl-, cyclobutylmethyl-, cyclopentylmethyl-, cyclohexylmethyl-, cycloheptylmethyl-, cyclooctylmethyl-, 1-cyclopropylethyl-, 1-cyclobutylethyl-, 1-cyclopentylethyl-, 1-cyclohexylethyl-, 1-cycloheptylethyl-, 1-cyclooctylethyl-, 2-cyclopropylethyl-, 2-cyclobutylethyl-, 2-cyclopentylethyl-, 2-cyclohexylethyl-, 2-cycloheptylethyl-, 2-cyclooctylethyl-, 3-cyclopropylpropyl-, 3-cyclobutylpropyl-, 3-cyclopentylpropyl-, 3-cyclohexylpropyl-, 3-cycloheptylpropyl-, or 3-cyclooctylpropyl- in which groups the cycloalkyl subgroup as well as acyclic subgroup also can be unsaturated and/or substituted.

Of course, a group like $(C_1-C_8)$-alkyl is to be understood as comprising, among others, saturated acyclic $(C_1-C_8)$-alkyl, $(C_3-C_8)$-cycloalkyl, cycloalkyl-alkyl groups like $(C_3-C_7)$-cycloalkyl-$(C_1-C_5)$-alkyl- wherein the total number of carbon atoms can range from 4 to 8, and unsaturated $(C_2-C_8)$-alkyl like $(C_2-C_8)$-alkenyl or $(C_2-C_8)$-alkynyl. Similarly, a group like $(C_1-C_4)$-alkyl is to be understood as comprising, among others, saturated acyclic $(C_1-C_4)$-alkyl, $(C_3-C_4)$-cycloalkyl, cyclopropyl-methyl-, and unsaturated $(C_2-C_4)$-alkyl like $(C_2-C_4)$-alkenyl or $(C_2-C_4)$-alkynyl.

Unless stated otherwise, the term alkyl preferably comprises acyclic saturated hydrocarbon residues containing from 1 to 6 carbon atoms which can be linear or branched, acyclic unsaturated hydrocarbon residues containing from 2 to 6 carbon atoms which can be linear or branched like $(C_2-C_6)$-alkenyl and $(C_2-C_6)$-alkynyl, and cyclic alkyl groups containing from 3 to 8 ring carbon atoms, in particular from 3 to 6 ring carbon atoms. A particular group of saturated acyclic alkyl residues is formed by $(C_1-C_4)$-alkyl residues like methyl, ethyl, n-propyl, isopropyl, n-butyl, isobutyl, sec-butyl, and tert-butyl.

The alkyl groups of the present invention can in general be unsubstituted or substituted by one or more, for example, one, two, three, or four, identical or different substituents. Any kind of substituents present in substituted alkyl residues can be present in any desired position provided that the substitution does not lead to an unstable molecule. Examples of substituted alkyl residues are alkyl residues in which one or more, for example, 1, 2, 3, 4, or 5, hydrogen atoms are replaced with halogen atoms.

Examples of substituted cycloalkyl groups are cycloalkyl groups which carry as substituent one or more, for example, one, two, three, or four, identical or different acyclic alkyl groups, for example, acyclic $(C_1-C_4)$-alkyl groups like methyl groups. Examples of substituted cycloalkyl groups are 4-methylcyclohexyl, 4-tert-butylcyclohexyl, or 2,3-dimethylcyclopentyl.

Alkoxy as used herein means an alkyl-O— group in which the alkyl group is as previously described. Exemplary alkoxy groups include methoxy, ethoxy, n-propoxy, i-propoxy, n-butoxy, t-butoxy and polyethers including —O—$(CH_2)_2$ $OCH_3$.

The "heterocycle" group comprises groups containing 3, 4, 5, 6, 7, 8, 9, or 10 ring atoms in the parent monocyclic or bicyclic heterocyclic ring system. In monocyclic heterocycle groups, the heterocyclic ring preferably is a 3-membered, 4-membered, 5-membered, 6-membered, or 7-membered ring, particularly preferably, a 5-membered or 6-membered ring. In bicyclic heterocycle groups, preferably two fused rings are present, one of which is a 5-membered ring or 6-membered heterocyclic ring and the other of which is a 5-membered or 6-membered heterocyclic or carbocyclic ring, i.e., a bicyclic heterocycle ring preferably contains 8, 9, or 10 ring atoms, more preferably 9 or 10 ring atoms.

"Heterocycle" comprises saturated heterocyclic ring systems which do not contain any double bonds within the rings, as well as mono-unsaturated and poly-unsaturated heterocyclic ring systems which contain one or more, for example, one, two, three, four, or five, double bonds within the rings provided that the resulting system is stable. Unsaturated rings may be non-aromatic or aromatic, i.e., double bonds within the rings in the heterocycle group may be arranged in such a manner that a conjugated pi electron system results. Aromatic rings in a heterocycle group may be 5-membered or 6-membered rings, i.e., aromatic groups in a heterocycle group contain 5 to 10 ring atoms. Aromatic rings in a heterocycle group thus comprise 5-membered and 6-membered monocyclic heterocycles and bicyclic heterocycles composed of two 5-membered rings, one 5-membered ring, and one 6-membered ring, or two 6-membered rings. In bicyclic aromatic groups in a heterocycle group, one or both rings may contain heteroatoms. Aromatic heterocycle groups may also be referred to by the customary term heteroaryl for which all the definitions and explanations above and below relating to Heterocycle correspondingly apply.

Unless stated otherwise, in the heterocycle groups and any other heterocyclic groups, preferably 1, 2, 3, or 4 identical or different ring heteroatoms selected from nitrogen, oxygen, and sulfur are present. Particularly preferably, in these groups 1 or 2 identical or different ring heteroatoms selected from nitrogen, oxygen, and sulfur are present. The ring heteroatoms can be present in any desired number and in any position with respect to each other provided that the resulting heterocyclic system is known in the art and is stable and suitable as a subgroup in a drug substance. Examples of parent structures of heterocycles from which the heterocycle group can be derived are aziridine, oxirane, thiirane, azetidine, pyrrole, furan, thiophene, dioxole, imidazole, pyrazole, oxazole, isoxazole, thiazole, isothiazole, 1,2,3-triazole, 1,2,4-triazole, tetrazole, pyridine, pyran, thiopyran, pyridazine, pyrimidine, pyrazine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, azepine, 1,2-diazepine, 1,3-diazepine, 1,4-diazepine, indole, isoindole, benzofuran, benzothiophene, 1,3-benzodioxole, indazole, benzimidazole, benzoxazole, benzothiazole, quinoline, isoquinoline, chromane, isochromane, cinnoline, quinazoline, quinoxaline, phthalazine, pyridoimidazoles, pyridopyridines, pyridopyrimidines, purine, or pteridine, as well as ring systems which result from the listed heterocycles by fusion (or condensation) of a carbocyclic ring, for example, benzo-fused, cyclopenta-fused, cyclohexa-fused, or cyclohepta-fused derivatives of these heterocycles.

The heterocycle residue may be bonded via any ring carbon atom, and in the case of nitrogen heterocycles, via any suitable ring nitrogen atom. Thus, for example, a pyrrolyl residue can be 1-pyrrolyl, 2-pyrrolyl, or 3-pyrrolyl, a pyrrolidinyl residue can be 1-pyrrolidinyl (=pyrrolidino), 2-pyrrolidinyl, or 3-pyrrolidinyl, a pyridyl residue can be 2-pyridyl, 3-pyridyl, or 4-pyridyl, and a piperidinyl residue can be 1-piperidinyl (=piperidino), 2-piperidinyl, 3-piperidinyl, or 4-piperidinyl. Furyl can be 2-furyl or 3-furyl, thienyl can be 2-thienyl or 3-thienyl, imidazolyl can be 1-imidazolyl, 2-imidazolyl, 4-imidazolyl, or 5-imidazolyl, 1,3-oxazolyl can be 1,3-oxazol-2-yl, 1,3-oxazol-4-yl, or 1,3-oxazol-5-yl, 1,3-thiazolyl can be 1,3-thiazol-2-yl, 1,3-thiazol-4-yl, or 1,3-thiazol-5-yl, pyrimidinyl can be 2-pyrimidinyl, 4-pyrimidinyl (=6-pyrimidinyl), or 5-pyrimidinyl, and piperazinyl can be 1-piperazinyl (=4-piperazinyl=piperazino) or 2-piperazinyl. Indolyl can be 1-indolyl, 2-indolyl, 3-indolyl, 4-indolyl, 5-indolyl, 6-indolyl, or 7-indolyl. Similarly, benzimidazolyl, benzoxazolyl, and benzothiazolyl residues can be bonded via the 2-position and via any of the positions 4, 5, 6, and 7, benzimidazolyl also via the 1-position. Quinolyl can be 2-quinolyl, 3-quinolyl, 4-quinolyl, 5-quinolyl, 6-quinolyl, 7-quinolyl, or 8-quinolyl, and isoquinolyl can be 1-isoquinolyl, 3-isoquinolyl, 4-isoquinolyl, 5-isoquinolyl, 6-isoquinolyl, 7-isoquinolyl, or 8-isoquinolyl. In addition to being bonded via any of the positions indicated for quinolyl and isoquinolyl, 1,2,3,4-tetrahydroquinolyl and 1,2,3,4-tetrahydroisoquinolyl can also be bonded via the nitrogen atoms in the 1-position and 2-position, respectively.

Unless stated otherwise, and irrespective of any specific substituents bonded to heterocycle groups or any other heterocyclic groups which are indicated in the definition of compounds of the present invention, the heterocycle group can be unsubstituted or substituted on ring carbon atoms with one or more, for example, one, two, three, four, or five, identical or different substituents like $(C_1-C_8)$-alkyl, in particular $(C_1-C_4)$-alkyl, $(C_1-C_8)$-alkyloxy, in particular $(C_1-C_4)$-alkyloxy, $(C_1-C_4)$-alkylthio, halogen, nitro, amino, $((C_1-C_4)$-alkyl)carbonylamino like acetylamino, trifluoromethyl, trifluoromethoxy, hydroxy, oxo, hydroxy-$(C_1-C_4)$-alkyl such as, for example, hydroxymethyl, 1-hydroxyethyl, or 2-hydroxyethyl, methylenedioxy, ethylenedioxy, formyl, acetyl, cyano, methylsulfonyl, hydroxycarbonyl, aminocarbonyl, $(C_1-C_4)$-alkyloxycarbonyl, optionally substituted phenyl, optionally substituted phenoxy, benzyl optionally substituted in the phenyl group, or benzyloxy optionally substituted in the phenyl group. The substituents can be present in any desired position provided that a stable molecule results. Of course an oxo group cannot be present in an aromatic ring. Each suitable ring nitrogen atom in a heterocycle group can independently of each other be unsubstituted, i.e., carry a hydrogen atom, or can be substituted, i.e., carry a substituent like $(C_1-C_8)$-alkyl, for example, $(C_1-C_4)$-alkyl such as methyl or ethyl, optionally substituted phenyl, phenyl-$(C_1-C_4)$-alkyl, for example, benzyl, optionally substituted in the phenyl group, hydroxy-$(C_2-C_4)$-alkyl such as, for example, 2-hydroxyethyl, acetyl, or another acyl group, methylsulfonyl or another sulfonyl group, aminocarbonyl, or $(C_1-C_4)$-alkyloxycarbonyl. Nitrogen heterocycles can also be present as N-oxides or as quaternary salts. Ring sulfur atoms can be oxidized to the sulfoxide or to the sulfone. Thus, for example, a tetrahydrothienyl residue may be present as S,S-dioxotetrahydrothienyl residue or a thiomorpholinyl residue like 4-thiomorpholinyl may be present as 1-oxo-4-thiomorpholinyl or 1,1-dioxo-4-thiomorpholinyl. A substituted Heterocycle group that can be present in a specific position of compounds of formula I can independently of other heterocycle groups be substituted by substituents selected from any desired subgroup of the substituents listed before and/or in the definition of that group.

The explanations relating to the heterocycle residue correspondingly apply to divalent heterocycle residues including divalent heteroaromatic residues which may be bonded via any two ring carbon atoms and in the case of nitrogen heterocycles via any carbon atom and any suitable ring nitrogen atom or via any two suitable nitrogen atoms. For example, a pyridinediyl residue can be 2,3-pyridinediyl, 2,4-pyridinediyl, 2,5-pyridinediyl, 2,6-pyridinediyl, 3,4-pyridinediyl, or 3,5-pyridinediyl, a piperidinediyl residue can be, among others, 1,2-piperidinediyl, 1,3-piperidinediyl, 1,4-piperidinediyl, 2,3-piperidinediyl, 2,4-piperidinediyl, or 3,5-piperidinediyl, and a piperazinediyl residue can be, among others, 1,3-piperazinediyl, 1,4-piperazinediyl, 2,3-piperazinediyl, or 2,5-piperazinediyl.

Unless indicated otherwise, the term "amino" as used herein indicates a group linked to a nitrogen atom, such as, for example, alkylamino.

All compounds disclosed herein are assumed to include pharmaceutically acceptable salt forms. The term "pharmaceutically acceptable salt" as used herein is intended to include the non-toxic acid addition salts with inorganic or organic acids, e.g. salts with acids such as hydrochloric, phosphoric, sulfuric, maleic, acetic, citric, succinic, benzoic, fumaric, mandelic, p-toluene-sulfonic, methanesulfonic, ascorbic, lactic, gluconic, trifluoroacetic, hydroiodic, hydrobromic, and the like. Examples of pharmaceutically acceptable salts include, but are not limited to, mineral or organic acid salts of basic residues such as amines; alkali or organic salts of acidic residues such as carboxylic acids; and the like.

Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is hereby incorporated by reference.

The compounds of the present invention may be modified at least by (i) aromatization of 3-methyl-cyclohex-2-enol ring; dehydration (introduction of one more double bond) in 3-methyl-cyclohex-2-enol ring; modification of aliphatic chain that connects the rings (i.e. prolongation/shortening/branching), and/or modification of functional —OH group in the B ring (esters, ethers, halide, thiocyano, keto, cyano, amine).

The present invention also comprises all pharmaceutically acceptable compositions that comprise a compounds of the present invention. The definition of "pharmaceutically acceptable" is meant to encompass any carrier, which does not substantially interfere with effectiveness of the active ingredient and that is not toxic to the host to which it is administered. For example, for parenteral administration, the compounds of the present invention may be formulated in a unit dosage form for injection in vehicles such as saline, dextrose solution, etc. that may contain additives such as those that maintain stability.

The present invention also comprises methods of treating cancer comprising administering an anti-cancer agent, anti-cancer chemotherapy and/or anti-cancer radiation treatment; and administering a treatment enhancing amount of a compound of the present invention.

Another method of the present invention includes a method of inhibiting hypoxia-inducible factor-1 function in a patient or sample thereof, comprising administering to the patient or sample an effective inhibiting amount of a composition comprising a compound of the present invention.

Another method of the present invention is a method of enhancing a hypoxia-inducible factor-1 function inhibiting treatment in a patient or sample thereof, comprising administering to the patient or sample an HIF-1 inhibiting treatment; and administering to the patient or sample an effective treatment enhancing amount of a composition comprising a compound of the present invention.

Yet another method of the present invention is a method for treating a malignancy in a mammal, comprising administering a pharmaceutical compound or composition of the present invention with a therapy selected from the group consisting of radio immunoconjugate administration, other forms of radiopharmaceutical therapy, chemotherapy, external beam therapy, surgery, and other anti-malignancy treatment.

Finally, another method of the present invention is a method of treating cancer comprising (a) administering to a patient in need of such treatment, a pharmaceutically-effective amount of a composition of the present invention and (b) administering a therapy selected from radiation therapy and chemotherapy.

Hypoxia-regulated gene expression (selective activation and inactivation of genes) plays an important role in tumor cell adaptation to hypoxia and overall treatment resistance. The transcription factor HIF-1 is a key regulator of hypoxia-regulated gene expression. Compounds that can specifically regulate HIF-1 represent potential drug leads that will target tumor hypoxia and have little effect on well-oxygenated normal cells. Discovery efforts directed at finding specific functional antagonists of HIF-1 can lead to the identification of selective hypoxia/HIF-1 pathway inhibitors.

To identify functional antagonists of HIF-1, the present inventors have established a cell-based reporter assay for inhibitors of HIF-1 in hypoxia responsive human breast carcinoma T47D cells. Breast cancer was chosen as the target for this drug discovery effort, due to the high incidence of this disease and the urgent need to identify chemotherapeutic agents that target tumor hypoxia, the comprehensive knowledge base of breast cancer etiology, and the availability of well-studied human breast carcinoma cell lines as in vitro models. In addition, HIF-1α overexpression is associated with advanced stages of breast cancer and poor prognosis. The activity of HIF-1 is monitored using a luciferase reporter under the control of HRE from the erythropoietin gene (pTK-HRE3-luc). Natural product-rich extracts (dissolved in DMSO) are evaluated for activities that inhibit HIF-1 activation by hypoxia (about: 1% $O_2$/5% $CO_2$/94% $N_2$).

At a concentration of about 5 µg/ml, the crude extract (dichloromethane-methanol; 2:1) of the tropical red marine alga *Laurencia* sp. (conforms to *Laurencia intricata*) is found to strongly suppress hypoxia-induced HIF-1 activity in T47D breast carcinoma cells. Further examination reveals that the crude extract (identified in FIG. 1 as DNJ.006) inhibits HIF-1 activation by about 79% at about 1 µg/ml. Bioassay-guided fractionation as shown in FIG. 1 led to the discovery of a compound of the present invention. The structure of a compound of Formula (I) (also referred to by the inventors as LAURENDITERPENOL) is determined to be a structurally novel diterpene by a combination of spectroscopic and spectrometric means. In embodiments of the present invention, compounds of Formula (I) are substantially pure (preferably the compounds are at least about 90% pure).

Figure 2:
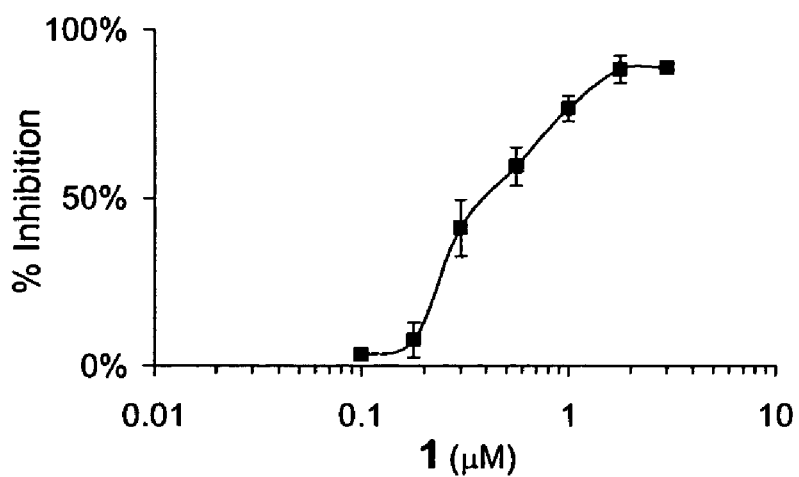
FIG. 2 is a graph that shows hypoxia-induced HIF-1 activity for a compound of formula 1, an embodiment of the present invention. The dose-response of a compound of formula 1 for inhibition of HIF-1 activation by hypoxia in T47D cells is shown. Results were analyzed using ANOVA and were found to be statistically significant, p, 0.05).
Figure 3:
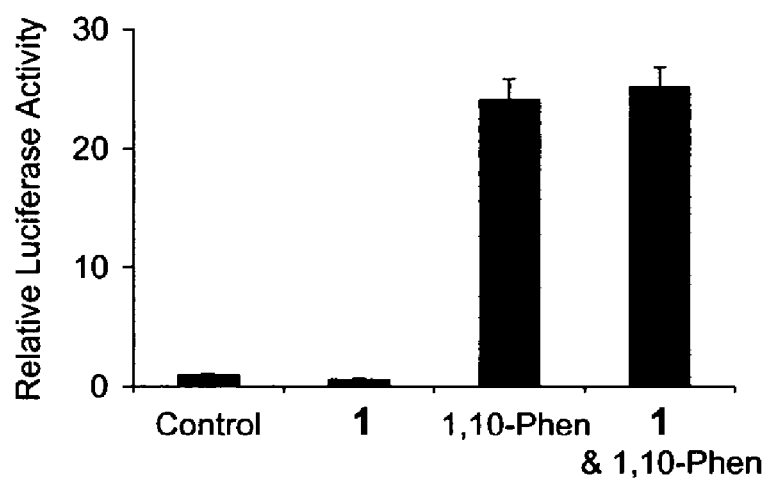
FIG. 3 is a bar graph that shows the effect of a compound of formula 1 (about 3 μM) on HIF-1 activation by a hypoxia mimetic 1,10-phenanthroline (about 10 μM) in T47D cells.
Figure 4:
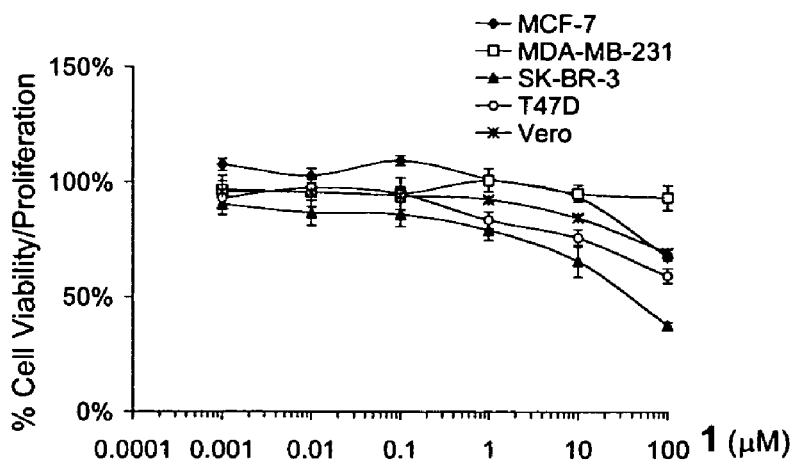
FIG. 4 shows the effects of a compound of formula 1 on cell proliferation/viability in a panel of cell lines.

As shown in FIG. 2, a compound of Formula (I) inhibits hypoxia-induced HIF-1 activity with an $IC_{50}$ of about 0.4 µM, but showed no statistically significant effect on iron chelator (1,10-phenanthroline at 10 µM)-induced HIF-1 (See FIG. 3). For these studies, exponentially grown T47D cells are transiently transfected with the pTK-HRE3-luc and pGL3-control (Promega) reporters and plated into 96-well plates. The pGL3-control reporter contains a modified reporter (cloned from *Photinus pyralis*) under the control of a SV40 early promoter and provides low-level, constitutive expression in mammalian cells as internal control.

About 24 hours after plating, a compound of Formula (I) is added to the transfected T47D cells. Following incubation at about 37° C. for about 30 minutes, the cells are exposed to hypoxic conditions (1% $O_2$/5% $CO_2$/94% $N_2$) or chemical hypoxia (iron chelator 1,10-phenanthroline at 10 µM) for 16 hr. At the end of incubation, the cells are harvested and both luciferase activities determined using a Luciferase Assay System (Promega). Luciferase activity from the pTK-HRE3-luc reporter was compared to luciferase activity from the pGL3-control reporter.

The data presented in FIGS. 2 and 3 are averages from one representative experiment performed in quadruplicate and the bars represent standard errors. Accordingly, a compound of Formula (I) is shown to have a selective effect on physiological hypoxia-induced HIF-1 activation, relative to "chemical hypoxia"-induced HIF-1. To rule out false positives associated with cytotoxicity, the effects of Formula (I) on cell viability are examined. Under similar hypoxic conditions, a compound of Formula (I) produces a marginal decrease in T47D cell viability measured by the Neutral Red assay.

As a master regulator of oxygen homeostasis, HIF-1 regulates the expression of many genes that promote cell survival and adaptation to hypoxia. One such HIF-1 target gene is VEGF, an important pro-angiogenic factor secreted by tumor cells to promote new blood vessel formation. Among cancer patients, increased VEGF protein level correlates with high microvessel density, advanced stage disease, and poor prognosis.

Figure 5:
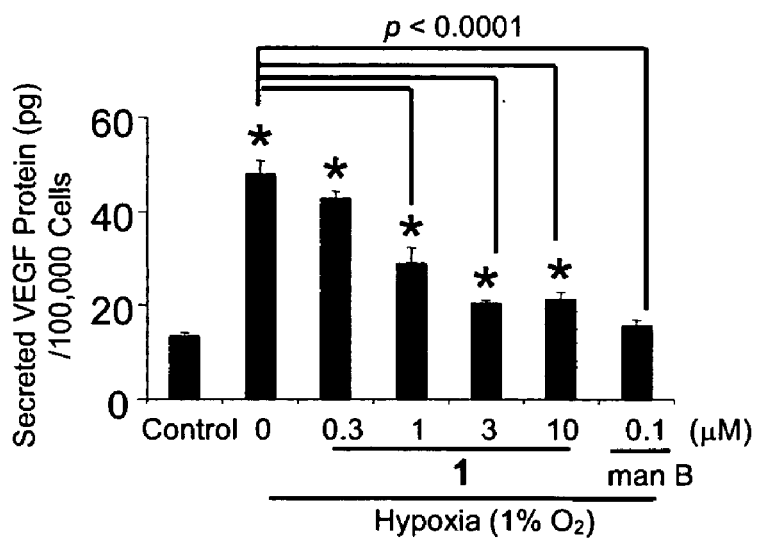
FIG. 5 is a graph that shows a compound of formula 1 inhibits the induction of secreted VEGF protein by hypoxia in T47D cells.
Figure 6:
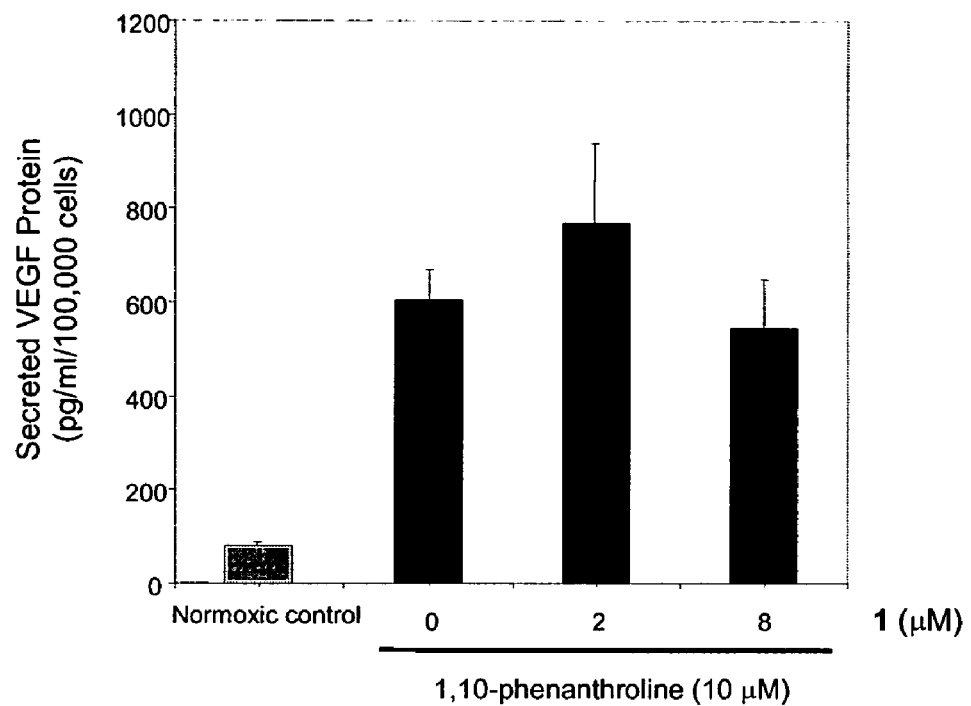
FIG. 6 is a graph that shows activity of a compound of the present invention with respect to the level of secreted VEGF protein levels in T47D cells that have been pretreated with 1,10-phenanthroline to induce hypoxia. This graph shows that the compound did not affect the induction of secreted VEGF protein.

Since secreted VEGF protein is the bioactive form, compounds that can reduce the level of secreted VEGF protein represent potential tumor angiogenesis inhibitors. Thus, compounds that can inhibit both hypoxic activation of HIF-1 and hypoxic induction of secreted VEGF protein represent "true" leads that target tumor hypoxia. The effects of compounds of the present invention on hypoxic induction of secreted VEGF protein are examined in T47D cells. Exponentially grown T47D cells were plated at the density of about 30,000 cells/well into 96-well plates. Compound treatment and hypoxic exposure were the same as described. Following incubation, secreted VEGF protein concentrations in the conditioned media are determined by ELISA (R & D Systems) and the data normalized by the number of viable cells. At concentrations of 1 µM and above, compounds of Formula (I) significantly decreases (by about 60%) the level of secreted VEGF protein produced following hypoxic treatment of T47D cells. See FIG. 5. The compounds of Formula (I) do not affect secreted VEGF protein levels in T47D cells that have been pretreated with 1,10-phenanthroline (to induce chemical hypoxia). See FIG. 6. Therefore, in addition to its effect on HIF-1, compounds of the present invention have a potential therapeutic application as an agent to inhibit tumor angiogenesis.

Figure 7:
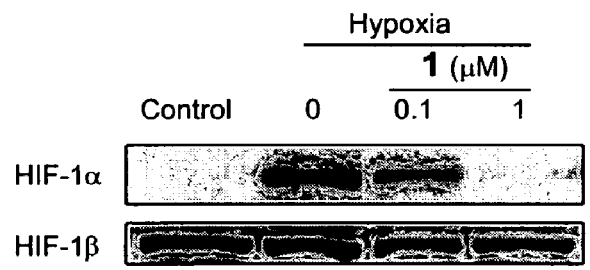
FIG. 7 shows the results of a Western blot showing a compound of the present invention with selective inhibition of the hypoxic induction of HIF-1a protein.
Figure 8:
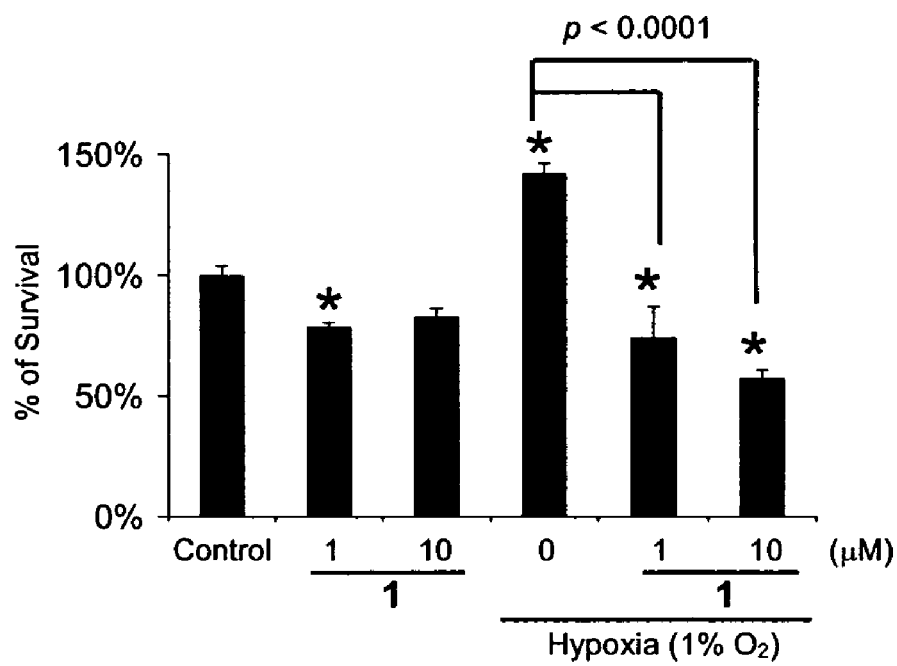
FIG. 8 is a graph showing that a compound of formula 1 significantly reduced T47D cell survival under hypoxic conditions.
Figure 9:
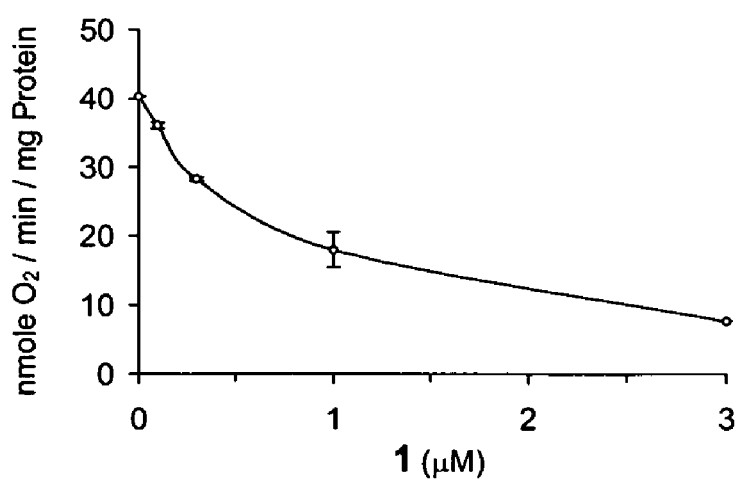
FIG. 9 is a graph showing that a compound of formula 1 inhibits the mitochondrial electron transport pathway. Mitochondrial oxygen consumption was measured, in this example, in the presence of glutamate/malate, ADP and increasing amounts of a compound of formula 1.

Since the availability of the oxygen-regulated HIF-1α protein determines the biological activity of HIF-1 and hypoxia induces HIF-1α protein, the effect of compounds of the present invention on the induction of HIF-1α protein are examined in T47D cells. Briefly, exponentially grown T47D cells are exposed to a compound of Formula (I) for about 30 minutes. The incubation then continues for about 4 hours under hypoxic conditions. Nuclear extracts are prepared from control and treated cells. The HIF-1α and HIF-1β proteins in the nuclear extract samples are detected by Western blot, using HIF-1α and HIF-1β specific antibodies (Novus Biologicals). Hypoxia induces nuclear HIF-1α protein without affecting the constitutively expressed HIF-1β protein and the compounds of the present invention specifically inhibit the hypoxic induction of HIF-1a protein (see FIG. 7). Significant inhibition of HIF-1α protein is observed at about 100 nM and complete inhibition is observed at about 1 µM. It is reasonable to conclude that the selectivity of the compounds of the present invention towards hypoxia-activated HIF-1 is caused by selective blockade of the hypoxic induction of HIF-1α protein.

In summary, no compound structurally related to the compounds of the present invention has been shown to inhibit HIF-1 activation or demonstrate antitumor activity. The compounds of the present invention selectively inhibit hypoxia-induced HIF-1 activity and, at similar concentrations, do not affect HIF-1 activation by agents that produce a state of "chemical hypoxia." The compounds of the present invention represent potential chemotherapeutic agents that target hypoxia and tumor angiogenesis.

REFERENCES CITED

The following publications, which primarily present background or supporting information, are incorporated herein by reference in its entirety, and are considered part of this disclosure.

1. Gibbs J B (2000) Mechanism-based target identification and drug discovery in cancer research. Science 287, 1969-1973.

2. Brown J M, Giaccia A J (1998) The unique physiology of solid tumors: opportunities (and problems) for cancer therapy. Cancer Res 58, 1408-1416.
3. Tomida A, Tsuruo T (1999) Drug resistance mediated by cellular stress response to the microenvironment of solid tumors. Anti-Cancer Drug Design 14, 169-177.
4. Brown J M (2000) Hypoxic cytotoxic agents: a new approach to cancer chemotherapy. Drug Resist Updat 3, 7-13.
5. von Pawel J, von Roemeling R, Gatzemeier U, Boyer M, Elisson L O, Clark P, Talbot D, Rey A, Butler T W, Hirsh V, Olver I, Bergman B, Ayoub J, Richardson G, Dunlop D, Arcenas A, Vescio R, Viallet J, Treat J (2000) Tirapazamine plus cisplatin versus cisplatin in advanced non-small-cell lung cancer: A report of the international CATAPULT I study group. Cisplatin and Tirapazamine in Subjects with Advanced Previously Untreated Non-Small-Cell Lung Tumors. J Clin Oncol 18, 1351-1359.
6. Saikumar P, Dong Z, Weinberg J M, Venkatachalam M A (1998) Mechanisms of cell death in hypoxia/reoxygenation injury. Oncogene 17, 3341-3349.
7. Graeber T G, Osmanian C, Jacks T, Housman D E, Koch C J, Lowe S W, Giaccia A J (1996) Hypoxia-mediated selection of cells with diminished apoptotic potential in solid tumours. Nature 379, 88-91.
8. Dachs G U, Tozer G M (2000) Hypoxia modulated gene expression: angiogenesis, metastasis and therapeutic exploitation. Eur J Cancer 36, 1649-1660.
9. Semenza G L (1999) Regulation of mammalian $O_2$ homeostasis by hypoxia-inducible factor 1. Annu Rev Cell Dev Biol 15, 551-578.
10. Semenza G L (2001) HIF-1, $O_2$, and the 3 PHDs: How animal cells signal hypoxia to the nucleus. Cell 107, 1-3.
11. Pugh C W, Gleadle J, Maxwell P H (2001) Hypoxia and oxidative stress in breast cancer. Hypoxia signalling pathways. Breast Cancer Res 3, 313-317.
12. Zhong H, De Marzo A M, Laughner E, Lim M, Hilton D A, Zagzag D, Buechler P, Isaacs W B, Semenza G L, Simons J W (1998) Overexpression of hypoxia-inducible factor 1 alpha in common human cancers and their metastases. Cancer Res 59, 5830-5835.
13. Bos R, Zhong H, Hanrahan C F, Mommers E C, Semenza G L, Pinedo H M, Abeloff M D, Simons J W, van Diest P J, van der Wall E (2001) Levels of hypoxia-inducible factor-1 alpha during breast carcinogenesis. J Natl Cancer Inst 93, 309-314.
14. Ryan H E, Lo J, Johnson R S (1998) HIF-1α is required for solid tumor formation and embryonic vascularization. EMBO J 17, 3005-3015.
15. Maxwell P H, Dachs G U, Gleadle J M, Nicholls L G, Harris A L, Stratford I J, Hankinson O, Pugh C W, Ratcliffe P J (1997) Hypoxia-inducible factor-1 modulates gene expression in solid tumors and influences both angiogenesis and tumor growth. Proc Natl Acad Sci USA 94, 8104-8109.
16. Jiang B H, Agani F, Passaniti A, Semenza G L (1997) V-SRC induces expression of hypoxia-inducible factor 1 (HIF-1) and transcription of genes encoding vascular endothelial growth factor and enolase 1: involvement of HIF-1 in tumor progression. Cancer Res 57. 5328-5335.
17. Ryan H E, Poloni M, McNulty W, Elson D, Gassmann M, Arbeit J M, Johnson R S (2000) Hypoxia-inducible factor-1 alpha is a positive factor in solid tumor growth. Cancer Res 60, 4010-4015.
18. Kung A L, Wang S, Klco J M, Kaelin W G, Livingston D M (2000) Suppression of tumor growth through disruption of hypoxia-inducible transcription. Nat Med 6, 1335-1340.
19. Cragg G M, Newman D J, Snader K M (1997) Natural Products in Drug Discovery and Development. J Nat Prod 60, 52-60.
20. Wang G L, Jiang B H, Semenza G L (1995) Effect of protein kinase and phosphatase inhibitors on expression of hypoxia-inducible factor 1. Biochem Biophys Res Commun 216, 669-675.
21. Richard D E, Berra E, Gothie E, Roux D, Pouyssegur J (1999) p42/p44 mitogen-activated protein kinases phosphorylate hypoxia-inducible factor 1 alpha (HIF-1 alpha) and enhance the transcriptional activity of HIF-1. J Biol Chem 274, 32631-32637.
22. Zhong H, Chiles K, Feldser D, Laughner E, Hanrahan C, Georgescu M M, Simons J W, Semenza G L (2000) Modulation of hypoxia-inducible factor 1 expression by the epidermal growth factor/phosphatidylinositol 3-kinase/PTEN/AKT/FRAP pathway in human prostate cancer cells: Implications for tumor angiogenesis and therapeutics. Cancer Res 60, 1541-1545.
23. Jiang B H, Jiang G, Zheng J Z, Lu Z, Hunter T, Vogt P K (2001) Phosphatidylinositol 3-kinase signaling controls levels of hypoxia-inducible factor 1. Cell Growth Differ 12, 363-369.
24. Gleadle J M, Ebert B L, Ratcliffe P J (1995) Diphenylene iodonium inhibits the induction of erythropoietin and other mammalian genes by hypoxia. Implications for the mechanism of oxygen sensing. Eur J Biochem 234, 92-99.
25. Chandel N S, Maltepe E, Goldwasser E, Mathieu C E, Simon M C, Schumacker P T (1998) Mitochondrial reactive oxygen species trigger hypoxia-induced transcription. Proc Natl Acad Sci USA 95, 11715-11720.
26. Liu Y, Christou H, Morita T, Laughner E, Semenza G L, Kourembanas S (1998) Carbon monoxide and nitric oxide suppress the hypoxic induction of vascular endothelial growth factor gene via the 5' enhancer. J Biol Chem 273, 15257-15262.
27. Huang L E, Willmore W G, Gu J, Goldberg M A, Bunn H F (1999) Inhibition of hypoxia-inducible factor 1 activation by carbon monoxide and nitric oxide. Implications for oxygen sensing and signaling. J Biol Chem 274, 9038-9044.
28. Wang G L, Semenza G L (1993) Characterization of hypoxia-inducible factor 1 and regulation of DNA binding activity by hypoxia. J Biol Chem 1993 268, 21513-21518.
29. Semenza G L, Wang G L (1992) A nuclear factor induced by hypoxia via de novo protein synthesis binds to the human erythropoietin gene enhancer at a site required for transcriptional activation. Mol Cell Biol 12, 5447-5454.
30. Rapisarda A, Uranchimeg B, Scudiero D A, Selby M, Sausville E A, Shoemaker R H, Melillo G (2002) Identification of small molecule inhibitors of hypoxia-inducible factor 1 transcriptional activation pathway. Cancer Res 62, 4316-4324.
31. Tian H, McKnight S L, Russell D W (1997) Endothelial PAS domain protein 1 (EPAS1), a transcription factor selectively expressed in endothelial cells. Genes Dev 11, 72-82.
32. Ferrrara N (1999) Role of vascular endothelial growth factor in regulation of angiogenesis. Antiangiogenic Agents in Cancer Therapy, edited by Teicher B A, Humana Press, New Jersey, pp 119-141.
33. Wang G L, Semenza G L (1993) Desferrioxamine induces erythropoietin gene expression and hypoxia-inducible factor 1 DNA-binding activity: implications for models of hypoxia signal transduction. Blood 82, 3610-3615.
34. Salnikow K, Su W, Blagosklonny M V, Costa M (2000) Carcinogenic metals induce hypoxia-inducible factor-stimulated transcription by reactive oxygen species-independent mechanism. Cancer Res 60, 3375-3378.
35. Bruick R K (2000) Expression of the gene encoding the proapoptotic Nip3 protein is induced by hypoxia. Proc Natl Acad Sci USA 97, 9082-9087.
36. Sowter H M, Ratcliffe P J, Watson P, Greenberg A H, Harris A L (2001) HIF-1-dependent regulation of hypoxic induction of the cell death factors BNIP3 and NIX in human tumors. Cancer Res 61, 6669-6673.
37. Cramer T, Yamanishi Y, Clausen B E, Förster I, Pawlinski R, Mackman N, Haase V H, Jaenisch R, Corr M, Nizet V, Firestein G S, Gerber H-P, Ferrara N, Johnson R S (2003) HIF-1 a Is Essential for Myeloid Cell-Mediated Inflammation. Cell 112, 645-657.
38 D'Amico D J (1994) "Diseases of the retina" *N. Engl. J. Med.* 331:95-106.
39. Aiello L P, Gardner T W, King G L, Blankenship G (1998) "Diabetic retinopathy" *Diabetes Care* 21:143-56.
40. National Eye Institute (1999) "Vision research—a national plan: 1999-2003" National Eye Institute, National Institute of Health.
41. Aiello L P (1997a) "Clinical implications of vascular endothelial growth factor in proliferative retinopathies" *Curr. Opin. Ophthalmol.* 8:19-31.
42. Aiello L P (1997b) "Vascular endothelial growth factor and the eye: biochemical mechanisms of action and implications for novel therapies" *Ophthalmic Res.* 29:354-63.
43. Miller J W (1997) "Vascular endothelial growth factor and ocular neovascularization" *Am. J. Pathol.* 151:13 23.
44. Aiello L P, Avery R L, Arrigg P G, Keyt B A, Jampel H D, Shah S T, Pasquale L R, Thieme H, Iwamoto M, Park J E, Nguyen H V, Aiello L M, Ferrara N, King G L (1994) "Vascular endothelial growth factor in ocular fluid of patients with diabetic retinopathy and other retinal dosorders" *N. Engl. J. Med.* 331:1480-7.
45. Ambati J, Chalam K V, Chawla D K, D'Angio C T, Guillet E G, Rose S J, Vanderlinde R E, Ambati B K (1997) "Elevated gamma-aminobutyric acid, glutamate, and vascular endothelial growth factor levels in the vitreous of patients with proliferative diabetic retinopathy" *Arch. Ophthalmol.* 115:1161-6.
46. Armstrong D, Augustin A J, Spengler R, Al-Jada A, Nickola T, Grus F, Koch F (1998) "Detection of vascular endothelial growth factor and tumor necrosis factor alpha in epiretinal membranes of proliferative diabetic retinopathy, proliferative vitreoretinopathy and macular pucker" *Ophthalmologica* 212:410-4.
47. Boulton M, Foreman D, Williams G, McLeod D (1998) "VEGF localisation in diabetic retinopathy" *Br. J. Ophthalmol.* 82:561-8.
48. Cao J, Mathews M K, McLeod DS, Merges C, Hjelmeland L M, Lutty G A (1999) "Angiogenic factors in human proliferative sickle cell retinopathy" *Br. J. Ophthalmol.* 83:838-46.
49. Pe'er J, Shweiki D, Itin A, Hemo I, Gnessin H, Keshet E (1995) "Hypoxia-induced expression of vascular endothelial growth factor by retinal cells is a common factor in neovascularizing ocular diseases" *Lab. Invest.* 72:638-45.
50. Kvanta A, Algvere P V, Berglin L, Seregard S (1996) "Subfoveal fibrovascular membranes in age-related macular degeneration express vascular endothelial growth factor" *Invest. Ophthalmol. Vis. Sci.* 37:1929 34.
51. Lopez P F, Sippy B D, Lambert H M, Thach A B, Hinton D R (1996) "Transdifferentiated retinal pigment epithelial cells are immunoreactive for vascular endothelial growth factor in surgically excised age-realted macular degeneration-related choroidal neovascular membranes" *Invest. Ophthalmol. Vis. Sci.* 37:855-68.
52. Kliffen M, Sharma H S, Mooy C M, Kerkyliet S, de Jong PTVM (1997) "Increased expression of angiogenic growth factors in age-related maculopathy" *Br. J. Ophthalmol.* 81:154-62.
53. Wessels M, Konig G M, Wright A (2000) "New Natural Product Isolation and Comparison of the Secondary Metabolite Content of Three Distinct Samples of the Sea Hare *Aplysia dactylomela* from Tererife" *J. Nat. Prod.* 63:920-928.
54. Harris A L (2002) "Hypoxia—a key regulatory factor in tumour growth" *Nat. Rev. Cancer* 2:38-47.
55. Semenza G L (2003) "Targeting HIF-1 for cancer therapy" *Nat. Rev. Cancer* 3:721-732.
56. Giaccia A, Siim B G, Johnson R S (2003) "HIF-1 as a target for drug development" *Nat. Rev. Drug Discov.* 2:803-11.
57. Unruh A, Ressel A, Mohamed H G, Johnson R S, Nadrowitz R, Richter E, Katschinski D M, Wenger R H (2003) "The hypoxia-inducible factor-1 alpha is a negative factor for tumor therapy" *Oncogene* 22:3213-3220.
58. Moeller B J, Cao Y, Li C Y, Dewhirst M W (2004) "Radiation activates HIF-1 to regulate vascular radiosensitivity in tumors: role of reoxygenation, free radicals, and stress granules" *Cancer Cell* 5:429-441.
59. Rischin D, Peters L, Fisher R, Macann A, Denham J, Poulsen M, Jackson M, Kenny L, Penniment M, Corry J, Lamb D, McClure B (2005) "Tirapazamine, Cisplatin, and Radiation versus Fluorouracil, Cisplatin, and Radiation in patients with locally advanced head and neck cancer: a randomized phase II trial of the Trans-Tasman Radiation Oncology Group (TROG 98.02)" *J. Clin. Oncol.* 23:79-87.
60. Mohammed K A, Hossain C F, Zhang L, Bruick R K, Zhou Y D, Nagle D G (2004) "Laurenditerpenol, a new diterpene from the tropical marine alga *Laurencia intricata* that potently inhibits HIF-1 mediated hypoxic signaling in breast tumor cells" J. Nat. Prod. 67:2002-2007.

The invention thus being described, it will be apparent to those skilled in the art that various modifications and variations can be made in the present invention without departing from the scope or spirit of the invention. All such modifications and variations are considered to be within the scope of the present invention and not a departure therefrom.

Unless otherwise specifically indicated, all numbers expressing quantities of ingredients, properties such as reaction conditions, and so forth used in the Specification and Claims are to be understood as being modified in all instances by the term "about." Accordingly, unless indicated to the contrary, the numerical parameters set forth in the Specification and Claims are approximations that may vary depending upon the desired properties sought to be determined by the present invention.

Notwithstanding that the numerical ranges and parameters setting forth the broad scope of the invention are approximations, the numerical values set forth in the experimental or example sections are reported as precisely as possible. Any numerical value, however, inherently contains certain errors necessarily resulting from the standard deviation found in their respective testing measurements.

Throughout this application, various publications are referenced. All such references are incorporated herein by reference.

We claim:

1. A compound of the following formula:

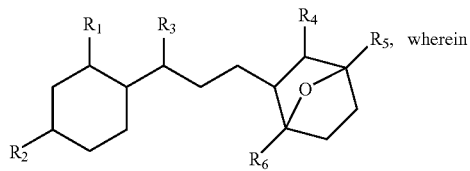 wherein $R_1$-$R_6$ are each independently H, alkyl, alkoxy, hydroxyl, heterocycle, amino;

and stereoisomers and pharmaceutically acceptable salts thereof.

2. A compound of claim 1, of the following formula:

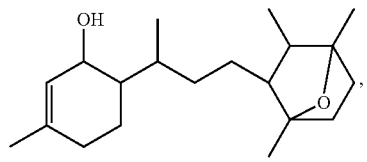

and stereoisomers thereof.

3. A pharmaceutical composition comprising a compound of claim 1, and stereoisomers thereof, and a pharmaceutically acceptable carrier.

4. A pharmaceutical composition comprising a compound of claim 2, and stereoisomers thereof, and a pharmaceutically acceptable carrier.

5. A method of inhibiting hypoxia-inducible factor-1 function in a patient or sample thereof, comprising:
administering to the patient or sample an effective inhibiting amount of a composition of claim 4.

6. A method of treating cancer in a subject, comprising:
administering an anti-cancer agent, anti-cancer chemotherapy and/or anti-cancer radiation treatment;
administering a chemotherapy or radiation treatment enhancing amount of a compound of claim 1 and a pharmaceutically acceptable carrier.

7. A method of treating cancer in a subject, comprising:
administering an anti-cancer agent, anti-cancer chemotherapy and/or anti-cancer radiation treatment;
administering a chemotherapy or radiation treatment enhancing amount of a compound of the following formula:

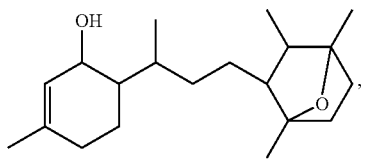

or a stereoisomer thereof, and a pharmaceutically acceptable carrier.

8. A method of enhancing a hypoxia-inducible factor-1 function inhibiting treatment in a patient or sample thereof, comprising:
administering to the patient or sample an HIF-1 inhibiting treatment; and
administering to the patient or sample an effective treatment enhancing amount of a composition comprising a compound of claim 1 and a pharmaceutically acceptable carrier.

9. A method of enhancing a hypoxia-inducible factor-1 function inhibiting treatment in a patient or sample thereof, comprising:
administering to the patient or sample an HIF-1 inhibiting treatment; and
administering to the patient or sample an effective treatment enhancing amount of a composition comprising a compound of the following formula:

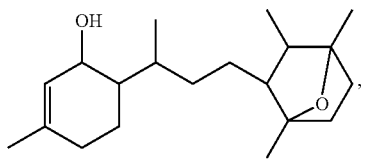

or a stereoisomer thereof, and a pharmaceutically acceptable carrier.

10. A method for treating a malignancy in a mammal, comprising administering a pharmaceutical composition of claim 3 in combination with a therapy selected from the group consisting of radioimmunoconjugate administration, other forms of radiopharmaceutical therapy, chemotherapy, external beam therapy, surgery, and other anti-malignancy treatment.

11. A method of treating cancer, said method comprising (a) administering to a patient in need of such treatment, a pharmaceutically-effective amount of a composition of claim 3, and (b) administering a therapy selected from radiation therapy and chemotherapy.

12. A method of inhibiting hypoxia-inducible factor-1 function to treat at least one of cancer, heart disease, stroke, macular degeneration, diabetic retinopathy, arthritis, comprising:
administering to the patient or sample an effective inhibiting amount of a composition of claim 4.

* * * * *